United States Patent
Richelsoph

(12) 
(10) Patent No.: US 6,432,110 B1
(45) Date of Patent: Aug. 13, 2002

(54) MODULAR TRIAL INSTRUMENT WITH INTERLOCK MECHANISM

(75) Inventor: Marc Evan Richelsoph, Memphis, TN (US)

(73) Assignee: Wright Medical Technology, Inc., Arlington, TN (US)

( * ) Notice: Subject to any disclaimer, the term of this patent is extended or adjusted under 35 U.S.C. 154(b) by 0 days.

(21) Appl. No.: 08/400,178

(22) Filed: Mar. 6, 1995

Related U.S. Application Data

(63) Continuation of application No. 08/143,391, filed on Oct. 29, 1993, now abandoned, which is a continuation of application No. 07/838,095, filed on Feb. 20, 1992, now abandoned.

(51) Int. Cl.[7] .............................................. A61B 17/56
(52) U.S. Cl. ...................................... 606/62; 623/23.11
(58) Field of Search .............................. 606/61, 62–68, 606/104; 623/18.11, 23.11, 23.15

(56) References Cited

U.S. PATENT DOCUMENTS

| | | | | |
|---|---|---|---|---|
| 3,067,740 A | * | 12/1962 | Haboush | 623/23 |
| 4,318,190 A | * | 3/1982 | Cortesi | 623/23 |
| 4,459,708 A | * | 7/1984 | Buttazzoni | 623/23 |
| 4,676,797 A | * | 6/1987 | Anapliotis | 623/23 |
| 4,687,486 A | * | 8/1987 | Brinckmann | 623/23 |
| 4,693,724 A | | 9/1987 | Rhenter et al. | |
| 4,995,883 A | * | 2/1991 | DeMane | 623/23 |
| 5,002,581 A | * | 3/1991 | Paxson | 623/23 |
| 5,032,130 A | * | 7/1991 | Schelhas | 623/23 |
| 5,035,717 A | * | 7/1991 | Brooks | 623/23 |
| 5,100,407 A | | 3/1992 | Conrad | |
| 5,108,437 A | * | 4/1992 | Kenna | 623/23 |
| 5,108,452 A | * | 4/1992 | Fallin | 623/23 |

* cited by examiner

*Primary Examiner*—Michael A. Brown
(74) *Attorney, Agent, or Firm*—Walker, McKenzie & Walker PC

(57) ABSTRACT

According to the present invention a modular trial instrument having opposed ends for sizing of an implantable orthopedic prosthesis is provided. The instrument comprises a head component located at one end of the trial and having at least one connection portion and a stem component located at the other end of the trial defining a longitudinal axis. The stem component includes a tip portion and a connection portion longitudinally opposed from the tip portion. The tip portion of stem component is received in the medullary canal of a bone. It will be apparent to those skilled in the art that the trial instrument can be used for sizing an implantable orthopedic prosthesis for any limb, for example, a humerus or a femur.

7 Claims, 2 Drawing Sheets

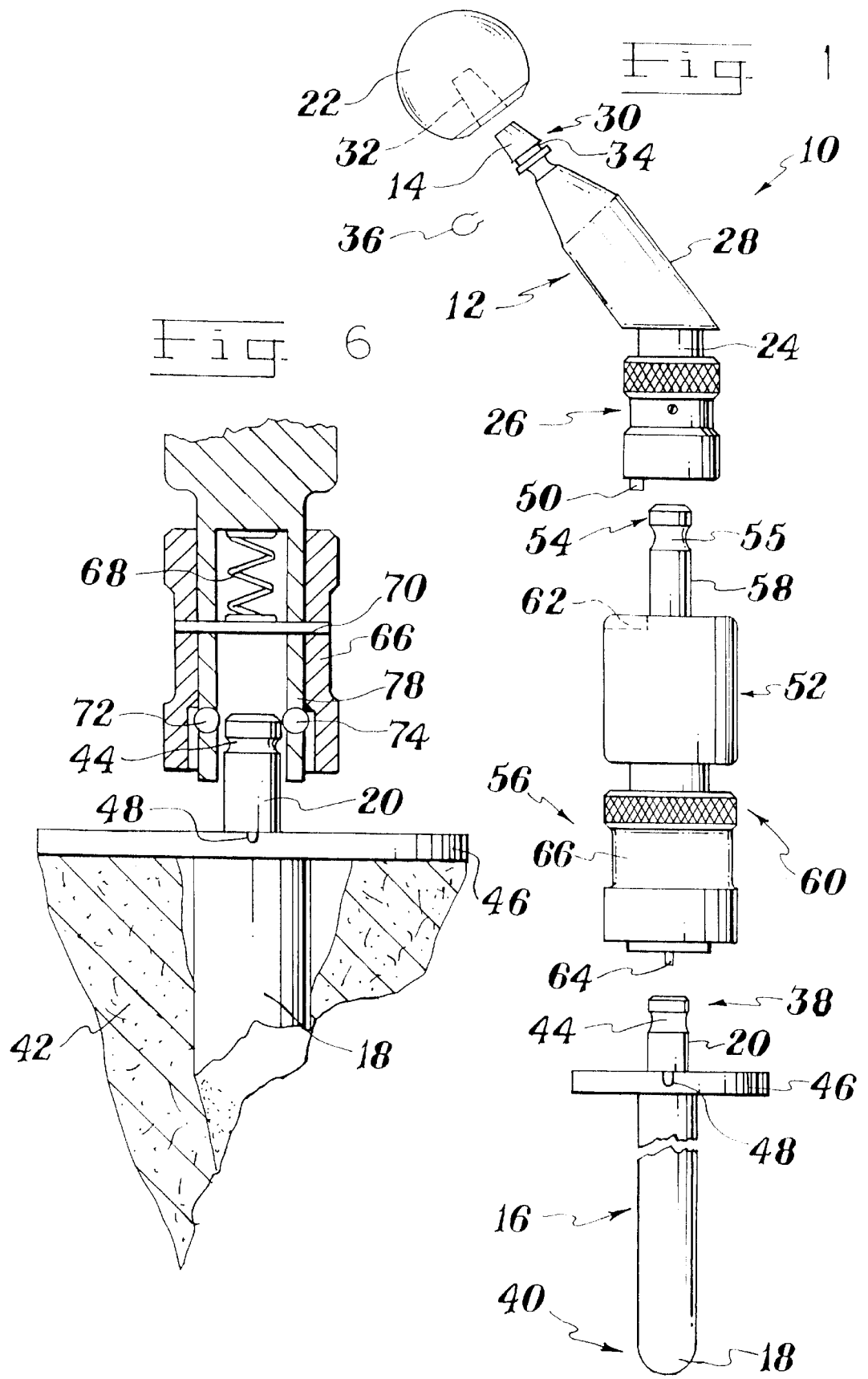

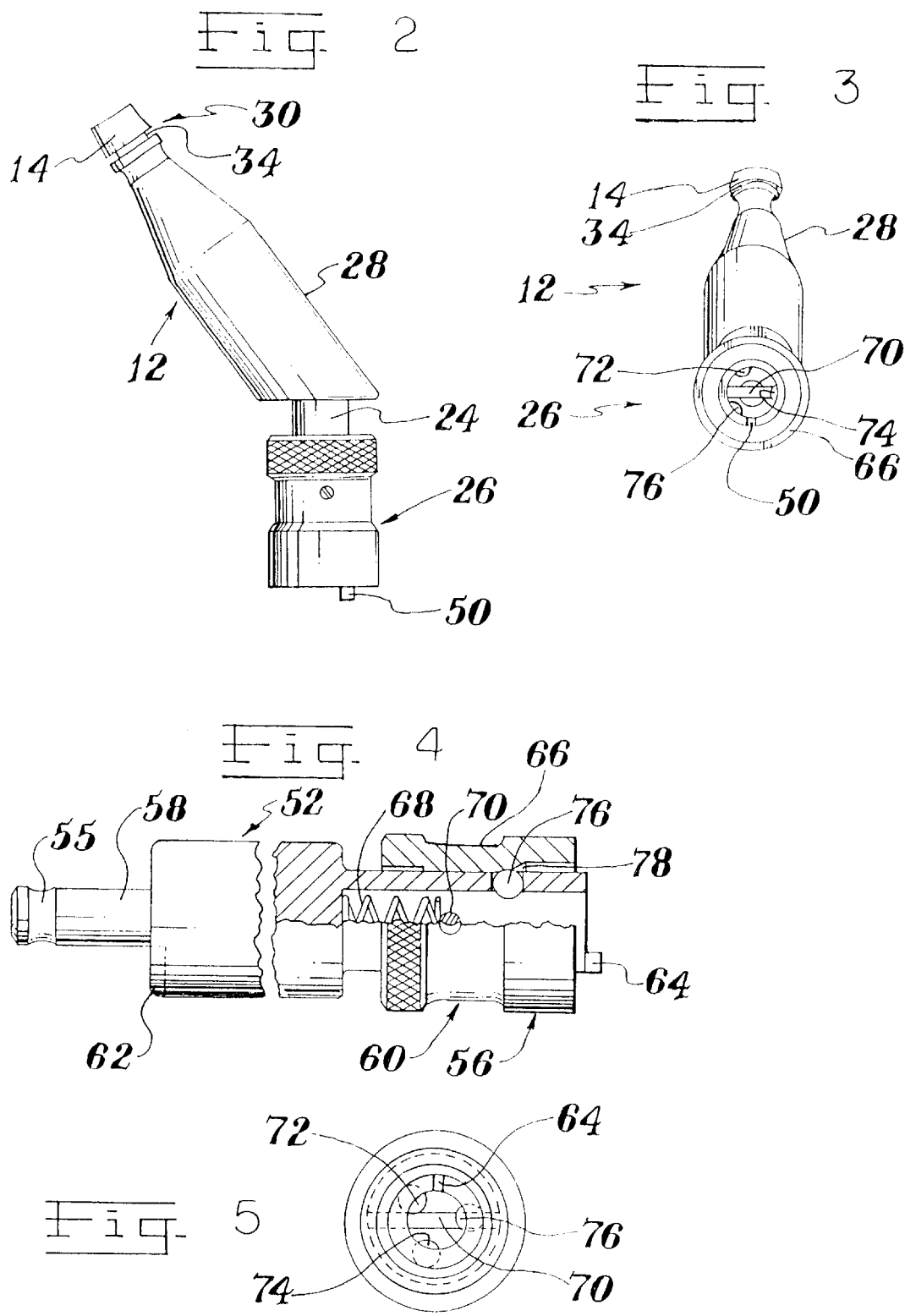

MODULAR TRIAL INSTRUMENT WITH INTERLOCK MECHANISM

This is a continuation of application Ser. No. 08/143,391, filed Oct. 29, 1993, now abandoned which is a continuation of now abandoned application, application Ser. No. 07/838,095, filed Feb. 20, 1992, both entitled "Modular Trial Instrument with Interlock Mechanism".

BACKGROUND OF THE INVENTION

1. Field of the Invention

The present invention relates to a trial for sizing replacement prosthesis for a portion of a bone. More particularly, the present invention relates to a modular trial for determining the size of a replacement prosthesis for a limb of the body.

2. Description of the Prior Art

Various prostheses have been designed to replace a portion of a bone joint. Generally a head portion is connected to an arm composed of a neck and a stem or shaft that will be embedded in the medullary canal of a bone for reconstruction. Such prostheses are often formed with an integral stem and neck portion, often a removable head element is positioned on the proximal end of the neck.

Recently modular structures fitted together from a number of replaceable parts that are available in a variety of sizes have been used. Using such prostheses it is possible to replace either the head portion or trochanteral portion of the prostheses, or both portions without removing the stem from the bone cavity. U.S. Pat. Nos. 4,676,797, and 4,693,724 are illustrative of such devices.

A disadvantage of the prostheses mentioned above is they limit the surgeon's ability to simply and quickly assemble the proper prosthesis components during a surgery and require using the actual prosthesis components for sizing, thus risking sterility of the prosthesis components.

SUMMARY OF THE INVENTION

According to the present invention a modular trial instrument having opposed ends for sizing of an implantable orthopedic prosthesis is provided. The instrument comprises a head component located at one end of the trial and having at least one connection portion and a stem component located at the other end of the trial defining a longitudinal axis. The stem component includes a tip portion and a connection portion longitudinally opposed from the tip portion. The tip portion of stem component is received in the medullary canal of a bone.

One advantage of the present invention is the trial preferably consists of components of various lengths and sizes that are adapted to be assembled together to form a custom trial for a prosthesis of a desired length and size. One advantage of this feature is that a trial of a desired length and size may be assembled at the during of the operation.

Another advantage of the present invention is the trial can be quickly and easily assembled and disassembled without the expenditure of special forces and the use of any tools.

Another advantage of the present invention is a modular trial is provided that allows a surgeon a great deal of flexibility as to the length and size of the trial.

Another advantage of the present invention is a surgeon may easily assemble a custom trial in the operating room before the prosthesis is inserted into the patient.

Yet another advantage of the present invention is a modular trial is provided that individual components can be assembled and disassembled, the prosthesis need not be rotated in screwing movements or the like, allowing the trial to be easily used in confined areas.

The modular trial of the present invention thus provides the ability to assemble and disassemble a number of components to produce a custom trial prosthesis by selecting different lengths and sizes of individual components to meet the requirements of the individual patient exactly.

BRIEF DESCRIPTION OF THE DRAWINGS

The invention may be better appreciated by reference to the attached Drawings, which illustrate one or more preferred embodiments, wherein:

FIG. 1 is an exploded perspective view of the modular trial instrument of this invention, FIG. 2 is a side view of the head component including the quick-disconnect, FIG. 3 is an end view showing quick-disconnect of the head component, FIG. 4 is a side view of the intermediate component including the quick-disconnect with parts broken away, FIG. 5 is an end view of the distal end of the intermediate component and the quick-disconnect, and FIG. 6 shows a cross sectional view of the quick-disconnect in conjunction with connection portion of a stem component inserted in the medullary canal of a bone.

DETAILED DESCRIPTION OF THE DRAWINGS

Referring to FIG. 1, a modular trial instrument having opposed ends for sizing of an implantable orthopedic prosthesis is generally shown at 10. The trial instrument comprises a head component 12 located at one end of the trial and having at least one connection portion 14. A stem component 16 is located at the other end of the trial defining a longitudinal axis. Stem component 16 includes tip portion 18 and connection portion 20 longitudinally opposed from the tip portion. The tip portion of stem component 16 is received in the medullary canal of a bone. It will be apparent to those skilled in the art that the trial instrument can be used for sizing an implantable orthopedic prosthesis for any limb, for example, a humerus or a femur.

Referring to FIGS. 1 and 2, a preferred embodiment of the modular trial instrument for orthopedic implantation of a hip prosthesis is generally shown at 10. The instrument comprises head component 12, stem component 16, and a ball indicated at 22. Head component 12 includes shaft 24 having one end attached to a releasable interlock mechanism, such as quick-disconnect 26 and the other end attached to neck portion 28. Neck portion 28 is generally cylindrical in cross-section and tapers to a smaller diameter towards proximal 30 end. Neck portion 28 is defined along a second axis forming an obtuse angle of about 35 degrees with the longitudinal axis, allowing a surgeon to rotate head component 12 180° about the longitudinal axis for a medial or lateral inclination. Various obtuse angles are possible for modify the medial or lateral inclination to accommodate the needs of the particular patient. Proximal 30 end of neck portion 28 is configured with connection portion 14 for mating with taper connection portion 32. Preferably the connection portions are of the Morse taper type. Connection portion 14 includes retaining groove 34 adapted to receive spring washer 36 for producing a friction fit as the connection portion is inserted into taper connection portion 32 of ball 22.

FIG. 3 shows end views of head portion 12 and quick-disconnect 26.

Referring to FIG. 1, stem component 16, having oppose proximal 38 and distal 40 ends, is located at the end of the trial defining a longitudinal axis. Stem 16 includes tip portion 18 and connection portion 20 longitudinally opposed from the tip portion. The tip portion is adapted to be received in the medullary canal of femur 42 as shown in FIG. 6. Various lengths of tip portion 18 are provided to correspond to the depth of the medullary canal of the femur. Connection portion 20 includes engagement groove 44 for releasably engaging quick-disconnect 26 of trial head 12. The connection 20 preferably consist of a cylindrical, non-tapered male portion as shown in FIGS. 1 and 6. Surrounding proximal 38 end is circumferential collar 46 for facilitating proper positioning of trial stem 16 in the medullary canal of femur 42. Axial slot 48 is formed in collar 46 for mating with tab 50 on quick-disconnect 26 to prevent rotation of stem 16 with respect to head 12.

With further reference to FIGS. 1 and 4, an intermediate component, generally indicated at 52, having a pair of interchangeable connection portions for mating engagement with another intermediate component, and with head 12 and stem 16 components, respectively. Intermediate component 52 defining the longitudinal axis includes opposed proximal 54 and distal 56 ends. Proximal 54 end is configured with connection portion 58 including engagement groove 55 for engaging quick-disconnect 26, and distal 56 end configured with quick-disconnect 60 for engaging connection portion 20 or the connection portion of another intermediate component. The connection portion 58 preferably consist of a cylindrical, non-tapered male portion as shown in FIGS. 1 and 4. Slot 62 is formed in the intermediate component for mating with tab 50 and tab 64 is provided for mating with slot 48. The tabs and slots when engaged prevent the components from rotating with respect to each other. A surgeon can selectively alter the length and size of trial by using various lengths and sizes of heads, stems and intermediate components depending on the needs of the patient, In FIG. 4, quick-disconnect 60 is shown with parts broken away and partially cross-sectioned. All of the quick-disconnects have the same structure and are interchangeable with one another. The quick-disconnect comprises slidable sleeve 66 encircling distal 56 end of intermediate component 52, internal spring 68 or similar means for urging sleeve 66 into the locked position, pin 70 mounted perpendicularly to the longitudinal axis of the sleeve and balls 72, 74, and 76. Pin 70 supports spring 68 and transfers the force of the spring to sleeve 66, urging it to remain in the locked position. The orientation of spring 68, pin 70 and balls 72, 74, and 76 is best viewed in FIGS. 5 and 6.

Referring to FIG. 6, the quick-disconnect for releasably engaging connection portions 20 and 58, or intermediate portion 52, as the case may be, is shown. As noted, engagement groove 44 encircles connection portion 20 near the end, and is adapted to receive balls 72, 74, and 76 situated in sleeve 66. The distal inner portion of sleeve 66 is provided with a portion of enlarged inner radius 78 that allows balls 72, 74, and 76 to move radially outward when sleeve 66 is raised into the position shown. When engagement groove 44 is aligned with the balls, sleeve 66 is lowered and the balls 72, 74, and 76 are forced into the engagement groove by the sleeve to couple the quick-disconnect to connection portion 20. The quick-disconnect can easily be uncoupled from connection portion 20 by sliding sleeve 66 upward, thus allowing balls 72, 74, and 76 to move outwardly out of engagement groove 44.

Other modifications of the trial of the present invention will become apparent to those skilled in the art from an examination of the above specification and drawings, Therefore, other variations of the present invention may be made which fall within the scope of the following Claims even though such variations were not specifically discussed above.

What is claimed is:

1. Modular trial instrumentation for determining the dimensions of a replacement prosthesis to be surgically implanted in the medullary canal of a bone of an individual patient during an operation to implant the replacement prosthesis, the modular trial instrumentation comprising:

(a) a plurality of trial head components of different dimensions, each of the trial head components including a quick disconnect mating connection portion; the quick disconnect mating connection portion of each trial head component including a female portion having a cavity and a spring loaded locking mechanism; the spring loaded locking mechanism of the quick disconnect mating connection portion of each trial head component having a locked position and an unlocked position; the spring loaded locking mechanism of the quick disconnect mating connection portion of each trial head component being normally urged to the locked position and being movable from the locked position to the unlocked position by hand without additional tools;

(b) a plurality of trial stem components of different dimensions, each of the trial stem components defining a longitudinal axis and including a tip portion and a quick disconnect portion longitudinally opposed from the tip portion, the tip portion adapted to be received within the medullary canal of a bone, the quick disconnect portion of each trial stem component including a male portion having a transverse groove; and (c) a trial intermediate component for allowing selected combinations of trial head components and trial stem components to be readily attached relative to one another and detached from one another by hand without additional tools to produce a custom trial prosthesis in the operating room by selecting different trial head components and trial stem components to meet the estimated requirements of the individual patient and by selectively altering the dimensions of the custom trial prosthesis during the operation using various combinations of trial head components and trial stem components to substantially meet the exact requirements of the individual patient;

the trial intermediate component including a male portion for extending into the female portion of a selected trial head component, the male portion of the trial intermediate component having a transverse groove for engagement by the spring loaded mechanism of the quick disconnect mating connection portion of the selected trial head component to lock the selected trial head component to the trial intermediate component when the male portion of the trial intermediate component is extended into the female portion of the selected trial head component and the spring loaded locking mechanism of the quick disconnect mating connection portion of the selected trial head component is in the locked position;

the trial intermediate component including a female portion having a cavity for receiving the male portion of a selected trial stem component; the female portion of the trial intermediate component including a spring loaded locking mechanism having a locked position and an unlocked position; the spring loaded locking mechanism of the female portion of the trial intermediate component being normally urged to the locked position and being movable from the locked position to the unlocked position by hand without additional tools; the spring loaded locking mechanism of the female portion of the trial intermediate component engaging the groove of the male portion of the selected trial stem component to lock the selected trial stem component to the trial intermediate component when the male portion of the selected trial stem component is extended into the female portion of the trial intermediate component and the spring loaded locking mechanism of the trial intermediate component is in the locked position.

2. Modular trial instrumentation for determining the dimensions of a replacement prosthesis to be surgically implanted in the medullary canal of a bone of an individual patient during an operation to implant the replacement prosthesis, the modular trial instrumentation comprising:

(a) a plurality of trial head components of different dimensions, each of the trial head components including a quick disconnect mating connection portion; the quick disconnect mating connection portion of each trial head component including a female portion having a cavity and a locking mechanism; the locking mechanism of the quick disconnect mating connection portion of each trial head component having a locked position and an unlocked position; the locking mechanism of the quick disconnect mating connection portion of each trial head component being normally urged to the locked position and being movable from the locked position to the unlocked position by hand without additional tools;

(b) a plurality of trial stem components of different dimensions, each of the trial stem components defining a longitudinal axis and including a tip portion and a quick disconnect portion longitudinally opposed from the tip portion, the tip portion adapted to be received within the medullary canal of a bone, the quick disconnect portion of each trial stem component including a male portion having a locking area; and (c) a trial intermediate component for allowing selected combinations of trial head components and trial stem components to be readily attached relative to one another and detached from one another by hand without additional tools to produce a custom trial prosthesis in the operating room by selecting different trial head components and trial stem components to meet the estimated requirements of the individual patient and by selectively altering the dimensions of the custom trial prosthesis during the operation using various combinations of trial head components and trial stem components to substantially meet the exact requirements of the individual patient;

the trial intermediate component including a male portion for extending into the female portion of a selected trial head component, the male portion of the trial intermediate component having a transverse area for engagement by the locking mechanism of the quick disconnect mating connection portion of the selected trial head component to lock the selected trial head component to the trial intermediate component when the male portion of the trial intermediate component is extended into the female portion of the selected trial head component and the locking mechanism of the quick disconnect mating connection portion of the selected trial head component is in the locked position;

the trial intermediate component including a female portion having a cavity for receiving the male portion of a selected trial stem component; the female portion of the trial intermediate component including a locking mechanism having a locked position and an unlocked position; the locking mechanism of the female portion of the trial intermediate component being normally urged to the locked position and being movable from the locked position to the unlocked position by hand without additional tools; the locking mechanism of the female portion of the trial intermediate component engaging the transverse area of the male portion of the selected trial stem component to lock the selected trial stem component to the trial intermediate component when the male portion of the selected trial stem component is extended into the female portion of the trial intermediate component and the locking mechanism of the trial intermediate component is in the locked position.

3. Modular trial instrumentation for determining the dimensions of a replacement prosthesis to be surgically implanted in the medullary canal of a bone of an individual patient during an operation to implant the replacement prosthesis and for producing a custom trial prosthesis to articulate with a coacting articulation surface of a joint of the individual patient during trial reduction of the joint, the modular trial instrumentation comprising:

(a) a plurality of trial head components of different dimensions, each of the trial head components having a proximal end and a distal end;

(b) a plurality of trial stem components of different dimensions, each of the trial stem components having a proximal end and a distal end and having a longitudinal axis; and (c) quick release interlock means for joining a selected trial head component to a selected trial stem component to produce a custom trial prosthesis, for allowing the custom trial prosthesis to be implanted in the medullary canal of the bone of the patient with the distal end of the selected trial stem component of the custom trial prosthesis received in the medullary canal of the bone, for then allowing the custom trial prosthesis to articulate with the coacting articulating surface of the joint of the individual patient during trial reduction of the joint to determine the fit of the custom trial prosthesis, and for then allowing the dimensions of the custom trial prosthesis to be altered using trial-and-error without requiring the distal end of the selected trial stem component to be removed from the medullary canal of the bone by allowing the selected trial head component to be separated from the selected trial stem component while the distal end of the selected trial stem component remains implanted in the medullary canal of the bone and by allowing another trial head component to be connected to the selected trial stem component while the distal end of selected trial stem component remains implanted in the medullary canal of the bone; the quick release interlock means including means for allowing the selected trial head component to be disconnected from the selected trial stem component in a direction along the longitudinal axis of the selected trial stem component.

4. The modular trial instrumentation of claim 3 in which the bone has a proximal end, and in which each of the trial stem components includes collar means for engaging the proximal end of the bone when implanted in the medullary canal of the bone for facilitating proper positioning of the trial stem components with respect to the bone.

5. Modular trial instrumentation for determining the dimensions of a replacement prosthesis to be surgically implanted in the medullary canal of a bone of an individual patient during an operation to implant the replacement prosthesis and for articulating with a coacting articulation surface of a joint of the individual patient during trial reduction of the joint, the bone having a proximal end, the modular trial instrumentation comprising:

(a) a plurality of trial stem components of different dimensions, each of the trial stem components defining a longitudinal axis and including a tip portion, and a quick disconnect portion longitudinally opposed from the tip portion, the tip portion adapted to be received within the medullary canal of a bone, the quick disconnect portion of each trial stem component including a male portion having a transverse groove; each trial stem component including collar means for engaging the proximal end of the bone when received by the medullary canal of the bone for facilitating proper positioning of the trial stem components with respect to the bone; and (b) a plurality of trial head components of different dimensions, each of the trial head components including a quick disconnect mating connection portion; the quick disconnect mating connection portion of each trial head component including a female portion having a cavity for receiving the male portion of a selected trial stem component, and a spring loaded locking mechanism; the spring loaded locking mechanism of the quick disconnect mating connection portion of each trial head component having a locked position and an unlocked position; the spring loaded locking mechanism of the quick disconnect mating connection portion of each trial head component being normally urged to the locked position and being movable from the locked position to the unlocked position by hand without additional tools; the quick disconnect mating portion for allowing selected combinations of trial head components and trial stem components to be readily attached relative to one another and detached from one another by hand without additional tools, without the removal of the trial stem component from the medullary canal of a bone, to produce a custom trial prosthesis in the operating room by selecting different trial head components and trial stem components to meet the estimated requirements of the individual patient and by selectively altering the dimensions of the custom trial prosthesis during the operation using various combinations of trial head components and trial stem components to substantially meet the exact requirements of the individual patient; the spring loaded locking mechanism of the female portion of the selected trial head component engaging the groove of the male portion of the selected trial stem component to lock the selected trial stem component to the selected trial head component when the male portion of the selected trial stem component is extended into the female portion of the selected trial head component and the spring loaded locking mechanism of the selected trial head component is in the locked position.

6. A method of sizing a replacement prosthesis to be surgically implanted in the medullary canal of a bone of an individual patient during an operation to implant the replacement prosthesis; the method comprising the steps of:

(a) assembling a custom trial prosthesis from modular trial instrumentation including a plurality of trial head components of different dimensions, a trial stem component having a longitudinal axis, and connection means for joining one of the plurality of trial head components to the trial stem component;

(b) implanting the custom trial prosthesis by inserting the trial stem component into the medullary canal of the bone;

(c) reducing the joint to determine the fit of the custom trial prosthesis; and then (c) altering the dimensions of the custom trial prosthesis by disconnecting the trial head component from the trial stem component in a direction along the longitudinal axis of the trial stem component and then connecting another trial head component to the trial stem component in a direction along the longitudinal axis of the trial stem component while the trial stem component remains implanted in medullary canal of the bone.

7. The method of claim 6 in which the bone has a proximal end, and in which the trail stem component includes collar means, and in which the method includes the additional step of engaging the proximal end of the bone withthe collar means when the trial stem component is inserted into the medullary canal of the bone to facilitate proper positioning of the trail stem components with respect to the bone.

* * * * *